United States Patent
Hong et al.

(10) Patent No.: US 11,680,061 B2
(45) Date of Patent: Jun. 20, 2023

(54) CRYSTAL FORMS C AND E OF PYRAZIN-2(1H)-ONE COMPOUND AND PREPARATION METHOD THEREFOR

(71) Applicant: ZHANGZHOU PIEN TZE HUANG PHARMACEUTICAL CO., LTD., Fujian (CN)

(72) Inventors: Fei Hong, Zhangzhou (CN); Jinming Huang, Zhangzhou (CN); Longhui Gao, Zhangzhou (CN); Shicong Wang, Zhangzhou (CN); Tingting Yin, Zhangzhou (CN); Zhifei Fu, Shanghai (CN); Miaorong Luo, Shanghai (CN); Yang Zhang, Shanghai (CN); Jian Li, Shanghai (CN); Shuhui Chen, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 0 days.

(21) Appl. No.: 17/633,319

(22) PCT Filed: Aug. 4, 2020

(86) PCT No.: PCT/CN2020/106896
§ 371 (c)(1),
(2) Date: Feb. 7, 2022

(87) PCT Pub. No.: WO2021/023194
PCT Pub. Date: Feb. 11, 2021

(65) Prior Publication Data
US 2022/0289722 A1      Sep. 15, 2022

(30) Foreign Application Priority Data

Aug. 8, 2019 (CN) .......... 201910731661.4
Nov. 1, 2019 (CN) .......... 201911059969.5

(51) Int. Cl.
*C07D 403/14* (2006.01)

(52) U.S. Cl.
CPC ........ *C07D 403/14* (2013.01); *C07B 2200/13* (2013.01)

(58) Field of Classification Search
CPC .................................................. C07D 403/14
See application file for complete search history.

(56) References Cited

U.S. PATENT DOCUMENTS

| | | | |
|---|---|---|---|
| 11,286,248 B2 * | 3/2022 | Zhang .................. | C07D 401/14 |
| 2013/0267525 A1 | 10/2013 | Saxty et al. | |
| 2017/0290839 A1 | 10/2017 | Lu et al. | |
| 2021/0040070 A1 | 2/2021 | Zhang et al. | |
| 2022/0315559 A1 | 10/2022 | Yu et al. | |

FOREIGN PATENT DOCUMENTS

| | | |
|---|---|---|
| CN | 103370314 A | 10/2013 |
| CN | 107438607 A | 12/2017 |
| JP | 2021523875 A | 9/2021 |
| JP | 2022535624 A | 8/2022 |
| WO | 2009058076 A1 | 5/2009 |
| WO | WO-2017070708 A1 | 4/2017 |
| WO | 2019154364 A1 | 8/2019 |

OTHER PUBLICATIONS

Bouchot et al. Taianta, vol. 218, May 2020, pp. 1-9.*
International Search Report (English and Chinese) issued in International Patent Application No. PCT/CN2020/106896, dated Oct. 28, 2020; ISA/CN.
Written Opinion of the International Searching Authority (English and Chinese) issued in International Patent Application No. PCT/CN2020/106896, dated Oct. 28, 2020; ISA/CN.
Oct. 12, 2022 Extended European Search Report issued in International Patent Application No. PCT/CN2020/106896.
Aug. 2, 2022 Japanese First Office Action issued in Japanese Patent Application No. 2022507752.
Aug. 2, 2022 Japanese First Office Action issued in Japanese Patent Application No. 2022507752 EN Version.
Mar. 29, 2023 Chinese First Office Action issued in Chinese Patent Application No. 2020800545628.

* cited by examiner

*Primary Examiner* — Samira J Jean-Louis
(74) *Attorney, Agent, or Firm* — Harness, Dickey & Pierce, P.L.C.

(57) ABSTRACT

A crystal form of a pyrazin-2(1H)-one compound and a preparation method therefor. The present invention specifically related to a compound of formula (II) and a preparation method for a crystal form of the compound.

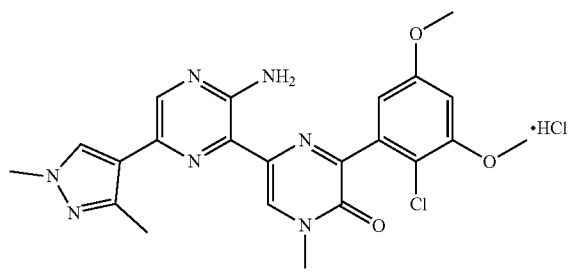

(II)

14 Claims, 4 Drawing Sheets

CRYSTAL FORMS C AND E OF PYRAZIN-2(1H)-ONE COMPOUND AND PREPARATION METHOD THEREFOR

CROSS-REFERENCE TO RELATED APPLICATIONS

This application is a U.S. National Phase Application under 35 U.S.C. 371 of International Application No. PCT/CN2020/106896, filed on Aug. 4, 2020, which claims the benefit of Chinese Patent Application No. 201910731661.4, filed on Aug. 8, 2019, and Chinese Patent Application No. 201911059969.5, filed on Nov. 1, 2019. The entire disclosures of the above applications are incorporated herein by reference.

TECHNICAL FIELD

The present disclosure relates to a crystal form of a pyrazin-2(1H)-one compound and a preparation method therefor, specifically relates to a preparation method of a compound of formula (II) and a crystal form thereof.

BACKGROUND

Fibroblast growth factor receptor (FGFR) is a receptor for fibroblast growth factor (FGF) signal transduction; the family of FGFR consists of four members (FGFR1, FGFR2, FGFR3, FGFR4), and FGFR is a glycoprotein consisting of an extracellular immunoglobulin (Ig)-like domain, a hydrophobic transmembrane region and an intracellular portion including a tyrosine kinase region. Fibroblast growth factor (FGF) plays an important role in many physiological regulatory processes such as cell proliferation, cell differentiation, cell migration and angiogenesis through these receptors (FGFR). There is much evidence linking FGF signaling pathway abnormalities (high expression, gene amplification, gene mutations, chromosomal reorganization, etc.) directly to many pathological processes such as tumor cell proliferation, migration, invasion, and angiogenesis. Therefore, FGFR has emerged as an important class of therapeutic targets that has attracted extensive research and development interest.

Content of the Present Invention

The present disclosure provides a hydrochloride salt of a compound of formula (I)

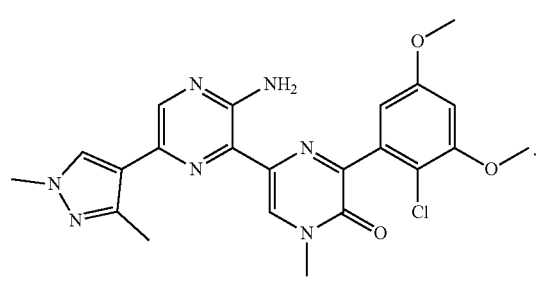

(I)

In some embodiments of the present disclosure, the hydrochloride salt of the compound of formula (I) has the structure shown in formula (III), wherein n is selected from 0.6 to 2.

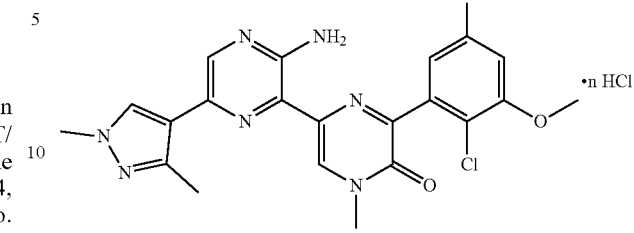

(III)

In some embodiments of the present disclosure, the n is selected from 0.6, 0.7, 0.8, 0.9, 1, 1.1, 1.2, 1.3, 1.4, 1.5, 1.6, 1.7, 1.8, 1.9, and 2.

In some embodiments of the present disclosure, then is selected from 0.9, 1, and 1.1.

In some embodiments of the present disclosure, the compound of formula (III) has the structure shown in formula (II)

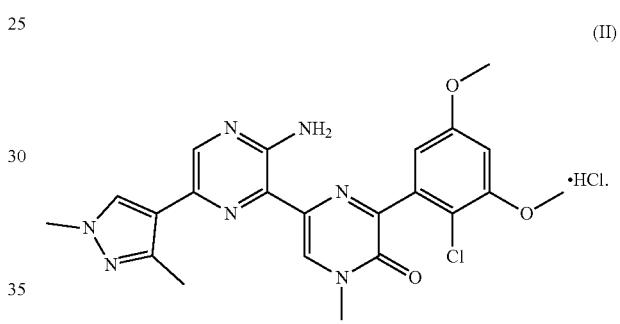

(II)

The present disclosure also provides a crystal form C of the compound of formula (II), and the X-ray powder diffraction pattern thereof comprises characteristic diffraction peaks at the following 2θ angles: 5.24±0.20°, 9.58±0.20°, and 10.45±0.20°.

In some embodiments of the present disclosure, the X-ray powder diffraction pattern of the crystal form C of the compound of formula (II) comprises characteristic diffraction peaks at the following 2θ angles: 5.24±0.20°, 9.58±0.20°, 10.45±0.20°, 14.25±0.20°, 20.86±0.20°, 24.99±0.20°, 26.21±0.20°, and 27.71±0.20°.

In some embodiments of the present disclosure, the X-ray powder diffraction pattern of the crystal form C of the compound of formula (II) comprises characteristic diffraction peaks at the following 2θ angles: 5.24±0.20°, 9.58±0.20°, 10.45±0.20°, 14.26±0.20°, 20.86±0.20°, 24.99±0.20°, 26.21±0.20°, and 27.71±0.20°.

In some embodiments of the present disclosure, the X-ray powder diffraction pattern of the crystal form C of the compound of formula (II) comprises characteristic diffraction peaks at the following 2θ angles: 5.24°, 8.45°, 9.08°, 9.58°, 10.45°, 11.49°, 13.23°, 14.02°, 14.26°, 15.18°, 15.60°, 16.35°, 18.15°, 18.74°, 19.52°, 19.94°, 20.86°, 21.65°, 21.97°, 22.50°, 23.28°, 23.64°, 24.16°, 24.99°, 26.21°, 26.98°, 27.71°, 28.52°, 29.07°, 29.43°, 30.37°, 31.72°, 32.30°, 33.11°, 34.79°, and 36.78°.

In some embodiments of the present disclosure, the XRPD pattern of the crystal form C of the compound of formula (II) is as shown in FIG. 1.

In some embodiments of the present disclosure, the analytical data of the XRPD pattern of the crystal form C of the compound of formula (II) are as shown in Table 1.

TABLE 1

Analytical data of the XRPD pattern of the crystal form C of the compound of formula (II)

| No. | Angle of 2θ (°) | d-Spacing (Å) | Relative intensity (%) |
|---|---|---|---|
| 1 | 5.240 | 16.8515 | 100.0 |
| 2 | 8.446 | 10.4606 | 1.5 |
| 3 | 9.083 | 9.7286 | 4.8 |
| 4 | 9.580 | 9.2247 | 31.6 |
| 5 | 10.448 | 8.4598 | 16.6 |
| 6 | 11.489 | 7.6957 | 5.0 |
| 7 | 13.231 | 6.6862 | 6.5 |
| 8 | 14.022 | 6.3109 | 7.4 |
| 9 | 14.256 | 6.2075 | 12.3 |
| 10 | 15.183 | 5.8307 | 7.2 |
| 11 | 15.600 | 5.6757 | 5.0 |
| 12 | 16.348 | 5.4176 | 3.5 |
| 13 | 18.146 | 4.8848 | 10.0 |
| 14 | 18.737 | 4.7320 | 5.0 |
| 15 | 19.523 | 4.5431 | 6.1 |
| 16 | 19.935 | 4.4502 | 5.9 |
| 17 | 20.861 | 4.2546 | 10.1 |
| 18 | 21.651 | 4.1012 | 2.8 |
| 19 | 21.970 | 4.0423 | 6.2 |
| 20 | 22.504 | 3.9477 | 3.0 |
| 21 | 23.284 | 3.8172 | 2.0 |
| 22 | 23.641 | 3.7603 | 2.0 |
| 23 | 24.158 | 3.6810 | 1.7 |
| 24 | 24.986 | 3.5608 | 11.7 |
| 25 | 26.210 | 3.3973 | 12.6 |
| 26 | 26.980 | 3.3021 | 8.2 |
| 27 | 27.707 | 3.2170 | 10.4 |
| 28 | 28.518 | 3.1273 | 2.6 |
| 29 | 29.071 | 3.0691 | 3.6 |
| 30 | 29.426 | 3.0329 | 2.3 |
| 31 | 30.372 | 2.9405 | 3.4 |
| 32 | 31.719 | 2.8187 | 2.2 |
| 33 | 32.305 | 2.7688 | 3.9 |
| 34 | 33.111 | 2.7033 | 5.3 |
| 35 | 34.786 | 2.5768 | 1.6 |
| 36 | 36.785 | 2.4413 | 2.3 |

In some embodiments of the present disclosure, the differential scanning calorimetry curve of the crystal form C of the compound of formula (II) has an endothermic peak with an onset at 216.4° C.±2.0° C., and has an endothermic peak with an onset at 258.8° C.±2.0° C.

In some embodiments of the present disclosure, the DSC pattern of the crystal form C of the compound of formula (II) is as shown in FIG. 2.

In some embodiments of the present disclosure, the thermogravimetric analysis curve of the crystal form C of the compound of formula (II) shows a weight loss of 0.1380% occurred at 118.6° C.±3.0° C., a weight loss of 6.7760% occurred at 205.5° C.±3.0° C., and a weight loss of 9.2750% occurred at 253.02° C.±3.0° C.

In some embodiments of the present disclosure, the TGA pattern of the crystal form C of the compound of formula (II) is as shown in FIG. 3.

The present disclosure also provides a crystal form E of the compound of formula (II), and the X-ray powder diffraction pattern thereof comprises characteristic diffraction peaks at the following 2θ angles: 9.05±0.20°, 10.36±0.20°, and 14.66±0.20°.

In some embodiments of the present disclosure, the X-ray powder diffraction pattern of the crystal form E of the compound of formula (II) comprises characteristic diffraction peaks at the following 2θ angles: 9.05±0.20°, 10.36±0.20°, 14.66±0.20°, 15.75±0.20°, 16.74±0.20°, 18.54±0.20°, 19.01±0.20°, 20.78±0.20°, 25.20±0.20°, and 26.65±0.20°.

In some embodiments of the present disclosure, the X-ray powder diffraction pattern of the crystal form E of the compound of formula (II) comprises characteristic diffraction peaks at the following 2θ angles: 9.05±0.20°, 10.36±0.20°, 14.66±0.20°, 15.75±0.20°, 16.74±0.20°, 18.54±0.20°, 25.20±0.20°, 26.65±0.20°, 27.28±0.20°, and 27.94±0.20°.

In some embodiments of the present disclosure, the X-ray powder diffraction pattern of the crystal form E of the compound of formula (II) comprises characteristic diffraction peaks at the following 2θ angles: 5.52°, 9.05°, 10.36°, 11.09°, 13.94°, 14.66°, 15.75°, 16.74°, 18.13°, 18.54°, 19.01°, 20.78°, 21.57°, 21.98°, 23.58°, 24.46°, 25.20°, 25.44°, 26.26°, 26.65°, 27.28°, 27.51°, 27.94°, 28.94°, 29.54°, 31.19°, 32.08°, 33.24°, 35.47°, 36.23°, 38.35°, and 39.34°.

In some embodiments of the present disclosure, the XRPD pattern of the crystal form E of the compound of formula (II) is as shown in FIG. 4.

In some embodiments of the present disclosure, the analytical data of the XRPD pattern of the crystal form E of the compound of formula (II) are as shown in Table 2.

TABLE 2

Analytical data of the XRPD pattern of the crystal form E of the compound of formula (II)

| No. | Angle of 2θ (°) | d-Spacing (Å) | Intensity | Relative intensity (%) |
|---|---|---|---|---|
| 1 | 5.52 | 16.01 | 226.78 | 6.77 |
| 2 | 9.05 | 9.77 | 3347.74 | 100.00 |
| 3 | 10.36 | 8.54 | 2325.54 | 69.47 |
| 4 | 11.09 | 7.98 | 575.72 | 17.20 |
| 5 | 13.94 | 6.35 | 431.88 | 12.90 |
| 6 | 14.66 | 6.04 | 1373.83 | 41.04 |
| 7 | 15.75 | 5.63 | 1030.20 | 30.77 |
| 8 | 16.74 | 5.30 | 842.46 | 25.17 |
| 9 | 18.13 | 4.89 | 233.95 | 6.99 |
| 10 | 18.54 | 4.78 | 894.13 | 26.71 |
| 11 | 19.01 | 4.67 | 1182.57 | 35.32 |
| 12 | 20.78 | 4.28 | 670.29 | 20.02 |
| 13 | 21.57 | 4.12 | 257.16 | 7.68 |
| 14 | 21.98 | 4.04 | 245.22 | 7.33 |
| 15 | 23.58 | 3.77 | 242.82 | 7.25 |
| 16 | 24.46 | 3.64 | 258.92 | 7.73 |
| 17 | 25.20 | 3.53 | 978.53 | 29.23 |
| 18 | 25.44 | 3.50 | 649.40 | 19.40 |
| 19 | 26.26 | 3.39 | 1196.59 | 35.74 |
| 20 | 26.65 | 3.35 | 1599.69 | 47.78 |
| 21 | 27.28 | 3.27 | 1400.84 | 41.84 |
| 22 | 27.51 | 3.24 | 1144.82 | 34.20 |
| 23 | 27.94 | 3.19 | 895.54 | 26.75 |
| 24 | 28.94 | 3.09 | 295.33 | 8.82 |
| 25 | 29.54 | 3.02 | 140.69 | 4.20 |
| 26 | 31.19 | 2.87 | 590.45 | 17.64 |
| 27 | 32.08 | 2.79 | 433.19 | 12.94 |
| 28 | 33.24 | 2.70 | 200.41 | 5.99 |
| 29 | 35.47 | 2.53 | 82.43 | 2.46 |
| 30 | 36.23 | 2.48 | 101.05 | 3.02 |
| 31 | 38.35 | 2.35 | 82.70 | 2.47 |
| 32 | 39.34 | 2.29 | 390.51 | 11.66 |

In some embodiments of the present disclosure, the differential scanning calorimetry curve of the crystal form E of the compound of formula (II) has an endothermic peak with an onset at 261.8° C.±2.0° C.

In some embodiments of the present disclosure, the DSC pattern of the crystal form E of the compound of formula (II) is as shown in FIG. 5.

In some embodiments of the present disclosure, the thermogravimetric analysis curve of the crystal form E of the compound of formula (II) shows a weight loss of 1.72% occurred at 150.0° C.±3.0° C., a weight loss of 8.34% occurred at 230.0° C.±3.0° C., and a weight loss of 9.41% occurred at 280.0° C.±3.0° C.

In some embodiments of the present disclosure, the TGA pattern of the crystal form E of the compound of formula (II) is as shown in FIG. 6.

The present disclosure also provides a use of the compound of formula (III), the compound of formula (II), the crystal form C and the crystal form E in the manufacture of a medicament for treating diseases related to FGFR.

Technical Effect

The crystal form E of the compound of formula (II) is stable and easy to form drugs. According to the experimental embodiments of the trifluoroacetate salt of the compound of formula (I), it can be seen that the crystal form E of the compound of formula (II) exhibits better inhibitory activity against wild-type FGFR, and the selectivity of FGFR2 and 3 against FGFR1 and 4 is higher. The pharmacokinetic index in mice of the crystal form E of the compound of formula (II) is good.

The crystal form C of the compound of formula (II) is stable and easy to form drugs. According to the experimental embodiments of the trifluoroacetate salt of the compound of formula (I), it can be seen that the crystal form C of the compound of formula (II) exhibits better inhibitory activity against wild-type FGFR, and the selectivity of FGFR2 and 3 against FGFR1 and 4 is higher. The pharmacokinetic index in mice of the crystal form C of the compound of formula (II) is good.

The trifluoroacetate salt of the compound of formula (I) exhibits better inhibitory activity against wild-type FGFR, and the selectivity of FGFR2 and 3 against FGFR1 and 4 is higher. The pharmacokinetic index in mice of the trifluoroacetate salt of the compound of formula (I) is good.

Definition and Description

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions of the embodiments of the present disclosure are carried out in a suitable solvent, and the solvent should be suitable for the chemical change of the present disclosure, and the reagents and materials required. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The following abbreviations are used in the present disclosure: eq refers to equivalent, equivalents; PE refers to petroleum ether; DMSO refers to dimethyl sulfoxide; MeOH refers to methanol; and TFA refers to trifluoroacetic acid.

The solvents used in the present disclosure are commercially available and the commercially available compounds use their vendor directory names. When the mixed solvents are added to the reaction solution, each solvent can be mixed first and then added to the reaction solution; or each solvent can be added to the reaction solution in turn and mixed in the reaction system.

Compounds are named according to conventional naming principles in the field or by ChemDraw® software, and the commercially available compounds use their vendor directory names.

X-ray Powder Diffractometer (XRPD) Method in the Present Disclosure

About 10 to 20 mg of the sample was subjected to XRPD detection.

Detailed XRPD parameters are as follows:
X-ray tube: Cu, k2, ($\lambda$=1.54056Å)
X-ray tube voltage: 40 kV, X-ray tube current: 40 mA
Divergence slit: 0.60 mm
Detector slit: 10.50 mm
Anti-scattering slit: 7.10 mm
Scanning range: 4-40 deg
Step size: 0.02 deg
Step time: 0.12 second
Rotation speed of sample tray: 15 rpm Differential Scanning Calorimeter (DSC) Method in the Present Disclosure Samples (0.5 to 1 mg) were placed in a DSC aluminum crucible for testing, and the method was: 25° C. to 300 or 350° C., 10° C./min.

Thermal Gravimetric Analyzer (TGA) Method in the Present Disclosure

Samples (2 to 5 mg) were placed in a TGA platinum crucible for testing, under the condition of 25 mL/min $N_2$ at a heating rate of 10° C./min, the sample was heated from room temperature to 300° C. or until a weight loss of 20%.

Dynamic Vapor Sorption (DVS) Method in the Present Disclosure

Instrument model: SMS DVS Advantage dynamic vapor sorption instrument

Test conditions: samples (10 mg to 15 mg) were placed in a DVS sample tray for testing.

Detailed DVS parameters are as follows:
Temperature: 25° C.
Balance: dm/dt=0.01%/min (shortest: 10 min, longest: 180 min)
Drying: 120 min under 0% RH
RH (%) test step: 10%
RH (%) test step range: 0% to 90% to 0%

The evaluation classification of hygroscopicity was as follows:

| Classification of hygroscopicity | ΔW % |
|---|---|
| Deliquescence | Absorbing sufficient water to form liquid |
| Highly hygroscopic | ΔW % > 15% |
| hygroscopic | 15% > ΔW % > 2% |

| Classification of hygroscopicity | ΔW % |
|---|---|
| Slightly hygroscopic | 2% > ΔW % > 0.2% |
| non-hygroscopic or almost non-hygroscopic | ΔW % < 0.2% |

Note:
ΔW % refers to the hygroscopic weight gain of the test samples at 25 ± 1° C. and 80 ± 2% RH.

DETAILED DESCRIPTION OF THE EMBODIMENT

Figure 1:
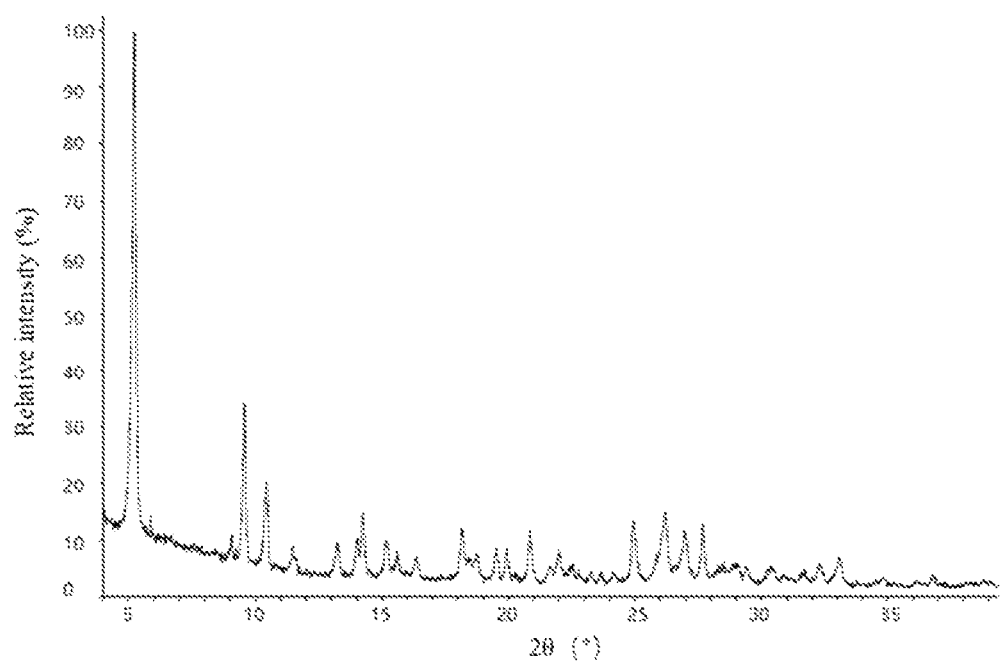
FIG. 1 is the XRPD pattern of the crystal form C of the compound of formula (II) measured by Cu-Kα radiation.
Figure 2:
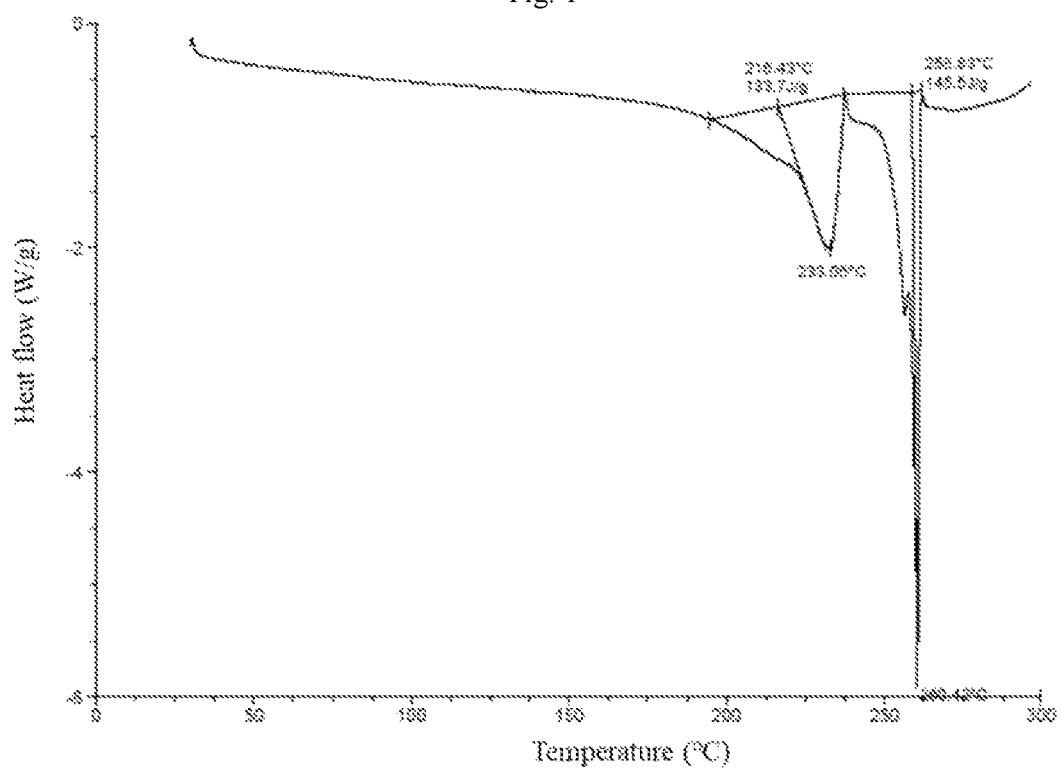
FIG. 2 is the DSC pattern of the crystal form C of the compound of formula (II).
Figure 3:
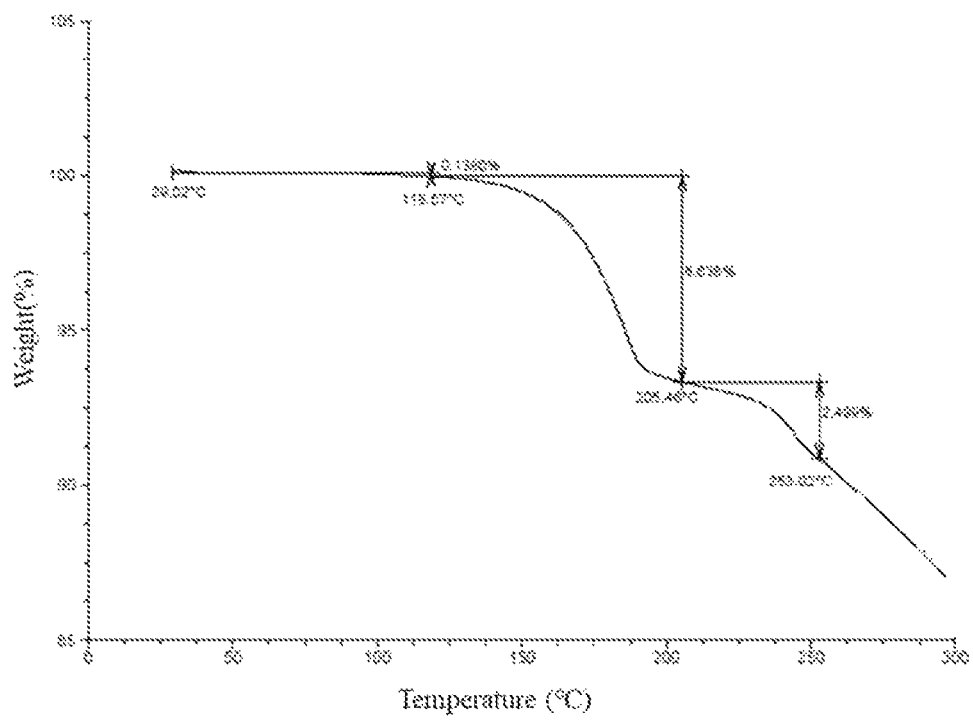
FIG. 3 is the TGA pattern of the crystal form C of the compound of formula (II).

The present disclosure is described in detail below by way of embodiments, but no adverse limitation of the disclosure is implied. The present disclosure has been described in detail herein, wherein specific embodiments thereof are also disclosed, and it will be apparent to those skilled in the art that various variations and improvements can be made to specific embodiments of the present disclosure without departing from the spirit and scope of the disclosure.

Embodiment 1: Preparation of the Compound of Formula (I) and the Trifluoroacetate Salt Thereof

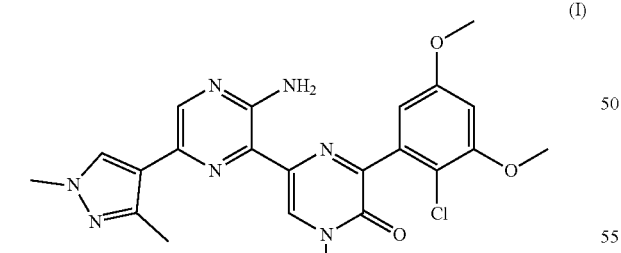

(I)

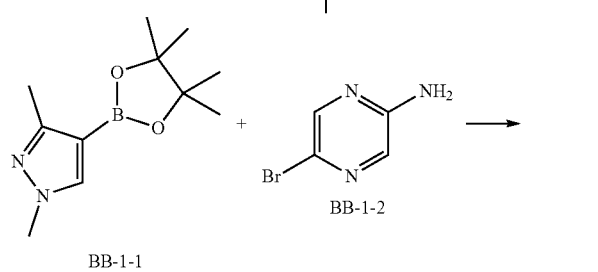

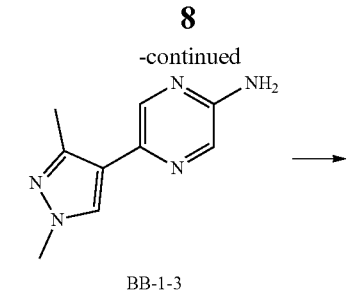

BB-1-3

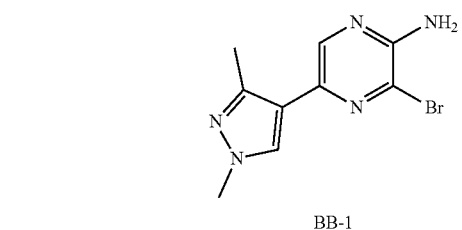

BB-1

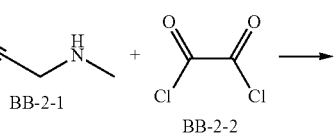

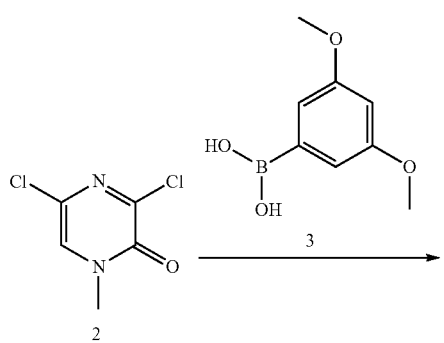

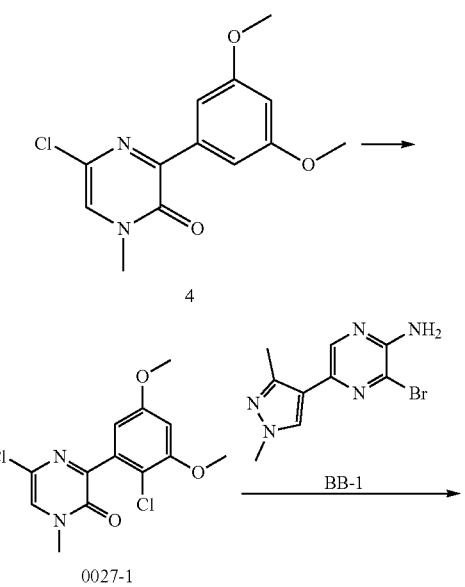

-continued

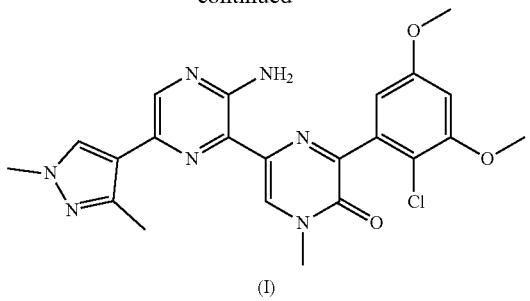

(I)

Step 1: Synthesis of Compound BB-1-3

Compound BB-1-2 (2.0 g, 11.49 mmol, 1 eq) and compound BB-1-1 (2.6 g, 11.49 mmol, 1 eq) were dissolved in water (6.0 mL) and dioxane (25.0 mL), followed by the addition of [1,1'-bis(diphenylphosphino)ferrocene] palladium dichloride (841 mg, 1.15 mmol, 0.1 eq) and potassium carbonate (4.8 g, 34.48 mmol, 3 eq), and the mixture was heated to 100° C. and reacted for 16 hours under the protection of nitrogen. The obtained reaction mixture was filtered under reduced pressure and evaporated to dryness by rotary evaporation, and the crude product was purified by column chromatography (petroleum ether:ethyl acetate=1:0 to 0:1) to obtain compound BB-1-3.

MS (ESI) m/z: 190.0[M+H]$^+$.

Step 2: Synthesis of Compound BB-1

Compound BB-1-3 (0.5 g, 2.64 mmol, 1 eq) and pyridine (209 mg, 2.64 mmol, 213.28 μL, 1 eq) were added to chloroform (20.0 mL), and the mixture was cooled to 0° C., and then bromine (422 mg, 2.64 mmol, 136.22 μL, 1 eq) was added thereto. The reaction was carried out at room temperature of 28° C. for 18 hours. The reaction was quenched with sodium thiosulfate (1.0 mL), then filtered under reduced pressure, and the filtrate was concentrated, and then the crude product was purified by flash silica gel column chromatography (petroleum ether:ethyl acetate=1:0 to 1:1). Compound BB-1 was obtained. MS (ESI) m/z: 267.9[M+H]$^+$.

$^1$H NMR (400 MHz, CD$_3$OD) δ: 8.12 (s, 1H), 7.90 (s, 1H), 3.86 (s, 3H), 2.43 (s, 3H).

Step 3: Synthesis of Compound 2

Under the protection of nitrogen, compound BB-2-1 (2.0 g, 18.77 mmol, 2.17 mL, 1 eq, HCl) was dissolved in chlorobenzene (15.0 mL), and then compound BB-2-2 (8.3 g, 65.69 mmol, 5.8 mL, 3.5 eq) was added dropwise at 25° C.; the mixture was slowly heated to 90° C. and stirred for 16 hours. Water (30.0 mL) and ethyl acetate (30.0 mL) were added to the reaction system, and the mixture was stood and then the layers were separated, and the aqueous phase was extracted three times with ethyl acetate (20.0 mL, 20.0 mL, 20.0 mL). The organic phases were combined, washed once with saturated sodium chloride solution (30.0 mL), and finally dried with anhydrous sodium sulfate, filtered and concentrated under reduced pressure. The crude product was separated and purified by column chromatography (petroleum ether:ethyl acetate=1:0 to 2:1) to obtain compound 2. MS (ESI) m/z: 178.7[M+1]$^+$.

$^1$H NMR (400 MHz, CDCl$_3$) δ: 7.26 (s, 1H), 3.61 (s, 3H).

Step 4: Synthesis of Compound 4

Compound 2 (0.2 g, 1.12 mmol, 1 eq) and compound 3 (213 mg, 1.17 mmol, 1.05 eq) were dissolved in a mixed solution of dioxane (1.5 mL) and water (1.5 mL) in a microwave tube under the protection of nitrogen, and tetrakis(triphenylphosphine)palladium (65 mg, 55.86 μmol, 0.05 eq) and sodium carbonate (130 mg, 1.23 mmol, 1.1 eq) were added, and the mixture was stirred at 120° C. for 30 minutes under microwave irradiation. The reaction mixture was concentrated directly. The crude product was separated by column chromatography (petroleum ether:ethyl acetate=1:0 to 0:1) (TLC detection petroleum ether:ethyl acetate=1:1) to obtain compound 4. MS (ESI) m/z: 281.0 [M+1]$^+$.

$^1$H NMR (400 MHz, CDCl$_3$) δ: 7.64 (d, 2H), 7.28 (s, 1H), 6.59 (t, 1H), 3.86 (s, 6H), 3.61 (s, 3H).

Step 5: Synthesis of Compound 0027-1

Compound 4 (250 mg, 890.61 μmol, 1 eq) was dissolved in a mixed solution of acetonitrile (20.0 mL) and dichloromethane (5.0 mL) under the protection of nitrogen; a solution of sulfonyl chloride (84 mg, 623.43 μmol, 62.33 μL, 0.7 eq) in acetonitrile (2.5 mL) was slowly added dropwise at 0° C., and the mixture was stirred at 0° C. for 10 minutes. The reaction was quenched by adding methanol (5.0 mL) to the reaction mixture and then the reaction mixture was concentrated to dryness under reduced pressure. The crude product was separated by column chromatography (petroleum ether:ethyl acetate=1:0 to 1:1) (TLC detection petroleum ether:ethyl acetate=1:1) to obtain compound 0027-1. MS (ESI) m/z: 314.9[M+H]$^+$.

Step 6: Synthesis of the Compound of Formula (I)

In a three-necked flask, compound 0027-1 (59 mg, 186.49 μmol, 1 eq), bis(pinacolato)diboron (52 mg, 205.14 μmol, 1.1 eq), palladium acetate (5 mg, 20.51 μmol, 0.11 eq), 2-dicyclohexylphosphino-2,4,6-triisopropylbiphenyl (20 mg, 41.03 μmol, 0.22 eq), and potassium acetate (60 mg, 615.42 μmol, 3.3 eq) were added to a solution of dioxane (4.0 mL); the air in the reaction system was replaced with nitrogen; under nitrogen saturation, the reaction system was raised to 100° C. and stirred under reflux for 30 min, cooled to 25° C., then compound BB-1 (50 mg, 186.49 μmol, 1 eq), dichloromethane complex of [1,1'-bis(diphenylphosphino) ferrocene] palladium dichloride (15 mg, 18.65 μmol, 0.1 eq), potassium carbonate (77 mg, 559.47 μmol, 3 eq), dioxane (4.0 mL) and water (2.0 mL) were added; the air in the reaction system was replaced with nitrogen; under nitrogen saturation, the temperature was raised to 100° C. and the mixture was stirred under reflux for 8 hours. The reaction mixture was concentrated directly. The obtained crude product was separated and purified by high performance liquid chromatography (chromatographic column: Boston Green ODS 150×30 mm 5 μm; mobile phase: [Water (0.1% TFA)-ACN]; B %: 30% to 60%, 8 min), and the trifluoroacetate salt of the compound of formula (I) was obtained. MS (ESI) m/z: 468.2[M+H]$^+$. $^1$H NMR (400 MHz, CD$_3$OD) δ: 8.79 (s, 1H), 8.09 (m, 2H), 6.76 (m, 2H), 3.93 (s, 3H), 3.89 (s, 3H), 3.84 (s, 3H), 3.80 (s, 3H), 2.54 (s, 3H). The salt was dissolved in dichloromethane, and the mixture was washed with saturated sodium carbonate; the organic phase was dried over anhydrous sodium sulfate, filtered, and the filtrate was evaporated to dryness by rotary evaporation to obtain the compound of formula (I). $^1$H NMR (400 MHz, CDCl$_3$) δ: 8.51 (s, 1H), 8.15 (s, 1H), 6.71 (d, J=2.8 Hz, 1H), 6.63 (d, J=2.8 Hz, 1H), 6.43 (brs, 2H), 3.94 (s, 3H), 3.92 (s, 3H), 3.84 (s, 3H), 3.79 (s, 3H), 2.55 (s, 3H).

Embodiment 2: Preparation of the Compound of Formula (II)

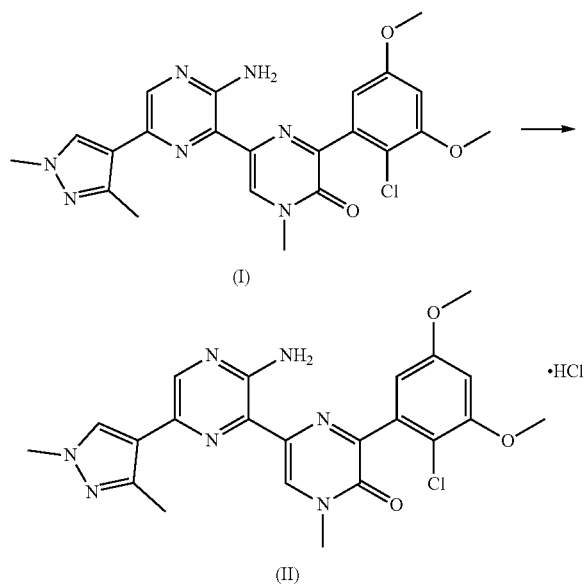

The compound of formula (I) (44.4 g, 94.89 mmol, 1 eq) was dissolved in tetrahydrofuran (450 mL), followed by the dropwise addition of a solution of hydrogen chloride (4 M, 94.89 mL, 4 eq) in ethyl acetate, and the mixture was stirred at 25° C. for 3 hours. The reaction mixture was filtered to obtain a yellow solid, which was pulled dry by an oil pump. The compound of formula (II) was obtained. $^1$H NMR (400 MHz, DMSO-d$_6$) δ: 8.71 (s, 1H), 8.18 (s, 2H), 6.82 (d, J=2.8 Hz, 1H), 6.75 (d, J=2.8 Hz, 1H) 3.91 (s, 3H), 3.81 (s, 3H), 3.80 (s, 3H), 3.71 (s, 3H), 2.44 (s, 3H).

Embodiment 3: Preparation of the Crystal Form C of the Compound of Formula (II)

400 mg of the compound of formula (II) was weighed and placed into a 40 mL glass flask, and 20 mL of ethyl acetate was added thereto, and then the mixture was stirred to form a suspension. The sample was placed on a magnetic stirrer (50° C.) and was stirred for 60 hours (protected from light). The sample was centrifuged quickly, and the residual solid was put into a vacuum drying oven, and vacuum-dried at 45° C. overnight to remove the residual solvent to obtain solid 1. Approximately 50 mg of solid 1 was weighed in a sample vial, and 1 mL of ethanol solvent was added, and the suspension was stirred continuously at 50° C. for 48 hours; after centrifugation, the residual solid was placed in a vacuum drying oven and dried overnight at 50° C. under vacuum to remove the residual solvent to obtain the crystal form C of the compound of formula (II).

Embodiment 4: Preparation of the Crystal Form E of the Compound of Formula (II)

6.6 L of ethanol was added to a 10 L three-necked glass flask, and the mixture was stared to stir. 330 g of the compound of formula (II) was added to the three-necked glass flask, and the temperature was raised to 45° C. and the stirring was continued for 48 hours. Buchner funnel was used for suction filtration, and the filter cake was leached with ethanol 200 mL×2. The filter cake was collected and dried in a vacuum drying oven at 50 to 55° C. for 14 to 20 hours to obtain the crystal form E of the compound of formula (II).

Embodiment 5: Study on the Hygroscopicity of the Crystal Form C of the Compound of Formula (II)

Experimental Materials:
SMS DVS Advantage Dynamic Vapor Sorption Instrument
Experimental Method:
10 to 15 mg of the crystal form C of the compound of formula (II) was placed in the DVS sample tray for testing.
Experimental Results:
The DVS pattern of the crystal form C of the compound of formula (II) is shown in the figure, ΔW=1.1%.
Experimental Conclusion:
At 25° C. and 80% RH, the hygroscopic weight gain of the crystal form C of the compound of formula (II) is 1.1%, which is slightly hygroscopic.

Embodiment 6: Study on the Hygroscopicity of the Crystal Form E of the Compound of Formula (II)
Experimental Materials:
SMS DVS Advantage Dynamic Vapor Sorption Instrument
Experimental Method:
10 to 15 mg of the crystal form E of the compound of formula (II) was placed in the DVS sample tray for testing.
Experimental Results:
The DVS pattern of the crystal form E of the compound of formula (II) is shown in the figure, ΔW=0.5%.
Experimental Conclusion:
At 25° C. and 80% RH, the hygroscopic weight gain of the crystal form E of the compound of formula (II) is 0.5%, which is slightly hygroscopic.

Experimental Embodiment 1: Evaluation of Wild-Type Kinase Inhibitory Activity In Vitro The IC$_{50}$ values were measured by $^{33}$P isotope-labeled kinase activity test (Reaction Biology Corp) to evaluate the inhibitory ability of the tested compounds on human FGFR1 and FGFR4.
Buffer conditions: 20 mM 4-(2-hydroxyethyl)-1-piperazineethanesulfonic acid (Hepes) (pH 7.5), 10 mM MgCl$_2$, 1 mM ethylene glycol-bis-(2-aminoethyl ether) tetraacetic acid (EGTA), 0.02% polyoxyethylene lauryl ether (Brij35), 0.02 mg/mL bovine serum albumin (BSA), 0.1 mM sodium vanadate (Na$_3$VO$_4$), 2 mM dithiothreitol (DTT), 1% DMSO.
Experimental steps: At room temperature, the tested compounds were dissolved in DMSO to prepare a 10 mM solution for later use. The substrate was dissolved in the freshly prepared buffer, and the tested kinase was added thereto and the mixture was mixed well. The DMSO solution dissolved with the tested compound was added to the above-mixed reaction mixture using acoustic technique (Echo 550). The concentrations of compounds in the reaction mixture were 10 μM, 3.33 μM, 1.11 μM, 0.370 M, 0.123 M, 41.2 nM, 13.7 nM, 4.57 nM, 1.52 nM, 0.508 nM, or 10 μM, 2.50 μM, 0.62 μM, 0.156 μM, 39.1 nM, 9.8 nM, 2.4 nM, 0.61 nM, 0.15 nM, 0.038 nM. After 15 minutes of incubation, $^{33}$P-ATP (activity 0.01 μCi/μL, corresponding concentrations listed in Table 3) was added to start the reaction. The supplier number, lot number and concentration information in the reaction mixture of FGFR1, FGFR4 and their substrates are listed in Table 3. After incubating the kinase reaction for 120 minutes at room temperature, the reaction mixture was deposited on P81 ion exchange filter paper (Whatman #3698-915). After repeatedly washing the filter paper with 0.75% phosphoric acid solution, the radioactivity of the phosphorylated substrate remaining on the filter paper was measured. The kinase activity data were expressed by the comparison of the kinase activity of the test compound with the kinase activity of the blank group (containing DMSO only). The $IC_{50}$ value was obtained by curve fitting with Prism4 software (GraphPad). The experimental results are shown in Table 4.

TABLE 3

Related information of kinase, substrate and ATP in test in vitro.

| Kinase | Supplier | Cat# | Lot # | ATP concentration (μM) |
|---|---|---|---|---|
| FGFR1 | Invitrogen | PV3146 | 28427Q | 5 |
| FGFR2 | Invitrogen | PV3368 | 315171 | 5 |
| FGFR3 | Invitrogen | PV3145 | 28459R | 30 |
| FGFR4 | Invitrogen | P3054 | 26967J | 2.5 |

| Substrate | Supplier | Cat# | Lot # | Concentration of substrate in reaction mixture (μM) |
|---|---|---|---|---|
| pEY (mg/mL) + Mn | Sigma | P7244-250MG | 062K5104V | 0.2 |
| pEY (mg/mL) + Mn | Sigma | P7244-250MG | 062K5104V | 0.2 |
| pEY (mg/mL) + Mn | Sigma | P7244-250MG | 062K5104V | 0.2 |
| pEY (mg/mL) + Mn | Sigma | P7244-250MG | 062K5104V | 0.2 |

TABLE 4

Results of in vitro screening tests for compounds of the present disclosure

| | $IC_{50}$ (nM) | | | | Selectivity | |
|---|---|---|---|---|---|---|
| Compound | FGFR1 | FGFR2 | FGFR3 | FGFR4 | FGFR1/2 | FGFR1/3 |
| The trifluoroacetate salt of the compound of formula (I) | 2.12 | 0.53 | 0.69 | 106 | 4.02 | 3.06 |

Conclusion: The trifluoroacetate salt of the compound of formula (I) exhibits better inhibitory activity against wild-type FGFR, and the selectivity of FGFR2 and 3 against FGFR1 and 4 is higher.

Experimental Embodiment 2: Pharmacokinetic Evaluation of Compounds

Experimental Purposes: To Test the Pharmacokinetics of the Compound in Mice

Experimental Materials:
CD-1 mice (male), vehicle (0.5% (w/v) methylcellulose 0.5% (v/v) Tween 80 aqueous solution), trifluoroacetate salt of compound 0027.
Preparation of Formulation for Administration:
The vehicle was 0.5% (w/v) methylcellulose and 0.5% (v/v) Tween 80 aqueous solution, and the formulation was prepared according to the following procedure:

a. About 50% volume of pure water was added to a suitable container and heated to about 60° C. to 70° C.

b. When the water temperature reached the specified value range, the heater was turned off. The required amount of methylcellulose was slowly added to the container and the mixture was stirred continuously.

c. The mixture was stirred continuously at 4° C. until the mixture was visually clarified.

d. The required volume of Tween 80 was added to the above solution. The mixture was stirred continuously until Tween 80 was uniformly dispersed and the mixture was visually clarified.

e. The above solution was fixed to a final volume with an appropriate amount of pure water.

f. The mixture was stirred continuously until a homogeneous solution was formed.

Preparation of formulation for intragastric administration:

a. An appropriate amount of the test product was weighed into a glass flask;

b. 70% volume of vehicle (0.5% (w/v) methylcellulose and 0.5% (v/v) Tween 80 aqueous solution) were added thereto;

c. the formulation was stirred until visually homogeneous, with water bath sonication when required;

e. the remaining volume of 0.5% methylcellulose and 0.5 Tween 80 were supplemented and the mixture was stirred uniformly.

Administration

Animals in groups 1 and 2 were given 5 mg/mL and 30 mg/mL compound by single intragastric administration, respectively, with a dose volume of 10 mL/kg.

The animals were weighed before administration, and the administration volume was calculated according to the body weight.

3. Sample Collection and Processing

Whole blood samples (30 μL) were collected at specified times (0.25, 0.5, 1, 2, 4, 6, 8, 24 hours) by saphenous vein collection and the actual time of collection was recorded in the test record. The acceptable error for the collection time points was ±1 minute for time points within 1 hour of administration and ±5% of the theoretical time for other time points.

All blood samples were immediately transferred to labeled commercial centrifuge tubes containing K2-EDTA. After blood samples were collected, the blood samples were centrifugated at 4° C. and 3200 rpm for 10 minutes, and the supernatant plasma was aspirated, and then quickly put into dry ice at a temperature of −20° C. or lower for LC-MS/MS analysis. And the pharmacokinetic parameters were calculated, experimental result: See Table 5.

TABLE 5

Results of the pharmacokinetics test

| | Compound The trifluoroacetate salt of the compound of formula (I) dosage | |
|---|---|---|
| Parameter | 50 mpk | 300 mpk |
| $C_{max}$ (nM) | 14800 | 42100 |
| $T_{max}$ (hr) | 1.00 | 7.00 |
| $T_{1/2}$ (hr) | 2.46 | ND |
| $T_{last}$ (hr) | ND | 24.0 |
| $AUC_{0-last}$ (nM · hr) | 85826 | 699413 |
| $AUC_{0-inf}$ (nM · hr) | 95847 | ND |

TABLE 5-continued

Results of the pharmacokinetics test

| Parameter | Compound The trifluoroacetate salt of the compound of formula (I) dosage | |
| --- | --- | --- |
| | 50 mpk | 300 mpk |
| $MRT_{0-last}$ (h) | 4.33 | 11.1 |
| $MRT_{0-inf}$ (h) | 5.39 | ND |

ND refers to: undetermined

Conclusion: The pharmacokinetic index of the trifluoroacetate salt of the compound of formula (I) in mice is good.

The invention claimed is:

1. A crystal form C of the hydrochloride salt as shown in formula (II), wherein the crystal form C has an X-ray powder diffraction pattern comprising characteristic diffraction peaks at the following 2θ angles: 5.24±0.20°, 9.58±0.20°, 10.45±0.20°, 14.26±0.20°, 20.86±0.20°, 24.99±0.20°, 26.21±0.20° and 27.71±0.20°,

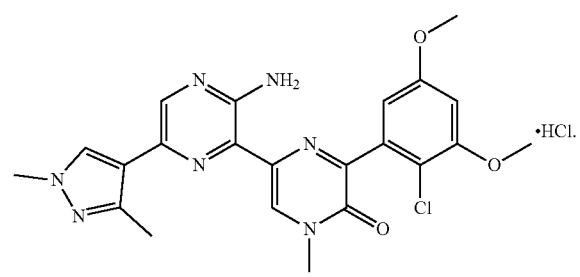

(II)

2. The crystal form C as defined in claim 1, wherein the X-ray powder diffraction pattern thereof comprises characteristic diffraction peaks at the following 2θ angles: 5.24°, 8.45°, 9.08°, 9.58°, 10.45°, 11.49°, 13.23°, 14.02°, 14.26°, 15.18°, 15.60°, 16.35°, 18.15°, 18.74°, 19.52°, 19.94°, 20.86°, 21.65°, 21.97°, 22.50°, 23.28°, 23.64°, 24.16°, 24.99°, 26.21°, 26.98°, 27.71°, 28.52°, 29.07°, 29.43°, 30.37°, 31.72°, 32.30°, 33.11°, 34.79° and 36.78°.

3. The crystal form C as defined in claim 2, wherein the X-ray powder diffraction pattern thereof is as shown in FIG. 1.

4. The crystal form C as defined in claim 1, wherein the crystal form C has a differential scanning calorimetry curve having an endothermic peak with an onset at 216.4° C.±2.0° C. and having an endothermic peak with an onset at 258.8° C.±2.0° C.

5. The crystal form C as defined in claim 1, wherein the crystal form C has a thermogravimetric analysis curve showing a weight loss of 0.1380% occurred at 118.6° C.±3.0° C., a weight loss of 6.7760% occurred at 205.5° C.±3.0° C. and a weight loss of 9.2750% occurred at 253.02° C.±3.0° C.

6. A crystal form E of the hydrochloride salt as shown in formula (II), wherein the crystal form E has an X-ray powder diffraction pattern comprising characteristic diffraction peaks at the following 2θ angles: 9.05±0.20°, 10.36±0.20°, and 14.66°,

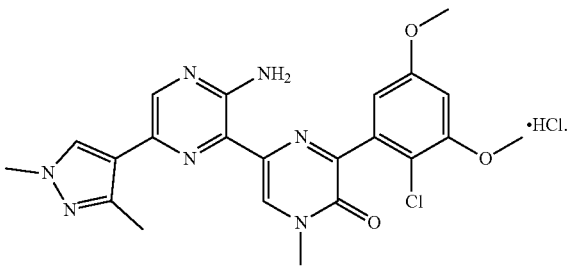

(II)

7. The crystal form E as defined in claim 6, wherein the X-ray powder diffraction pattern thereof comprises characteristic diffraction peaks at the following 2θ angles: 9.05±0.20°, 10.36±0.20°, 14.66±0.20°, 15.75±0.20°, 16.74±0.20°, 18.54±0.20°, 19.01±0.20°, 20.78±0.20°, 25.20±0.20°, and 26.65±0.20°.

8. The crystal form E as defined in claim 6, wherein the X-ray powder diffraction pattern thereof comprises characteristic diffraction peaks at the following 2θ angles: 9.05±0.20°, 10.36±0.20°, 14.66±0.20°, 15.75±0.20°, 16.74±0.20°, 18.54±0.20°, 25.20±0.20°, 26.65±0.20°, 27.28±0.20°, and 27.94±0.20°.

9. The crystal form E as defined in claim 7, wherein the X-ray powder diffraction pattern thereof comprises characteristic diffraction peaks at the following 2θ angles: 5.52°, 9.05°, 10.36°, 11.09°, 13.94°, 14.66°, 15.75°, 16.74°, 18.13°, 18.54°, 19.01°, 20.78°, 21.57°, 21.98°, 23.58°, 24.46°, 25.20°, 25.44°, 26.26°, 26.65°, 27.28°, 27.51°, 27.94°, 28.94°, 29.54°, 31.19°, 32.08°, 33.24°, 35.47°, 36.23°, 38.35°, 39.34°.

Figure 4:
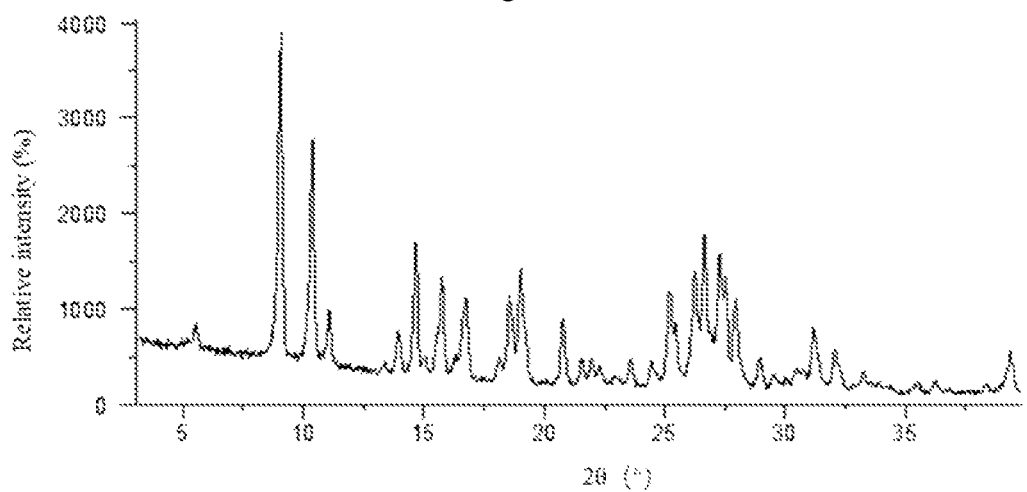
FIG. 4 is the XRPD pattern of the crystal form E of the compound of formula (II) measured by Cu-Kα radiation.

10. The crystal form E as defined in claim 9, wherein the XRPD pattern thereof is as shown in FIG. 4.

11. The crystal form E as defined in claim 7, wherein the crystal form E has a differential scanning calorimetry curve having an endothermic peak with an onset at 261.8° C.± 2.0° C.

Figure 5:
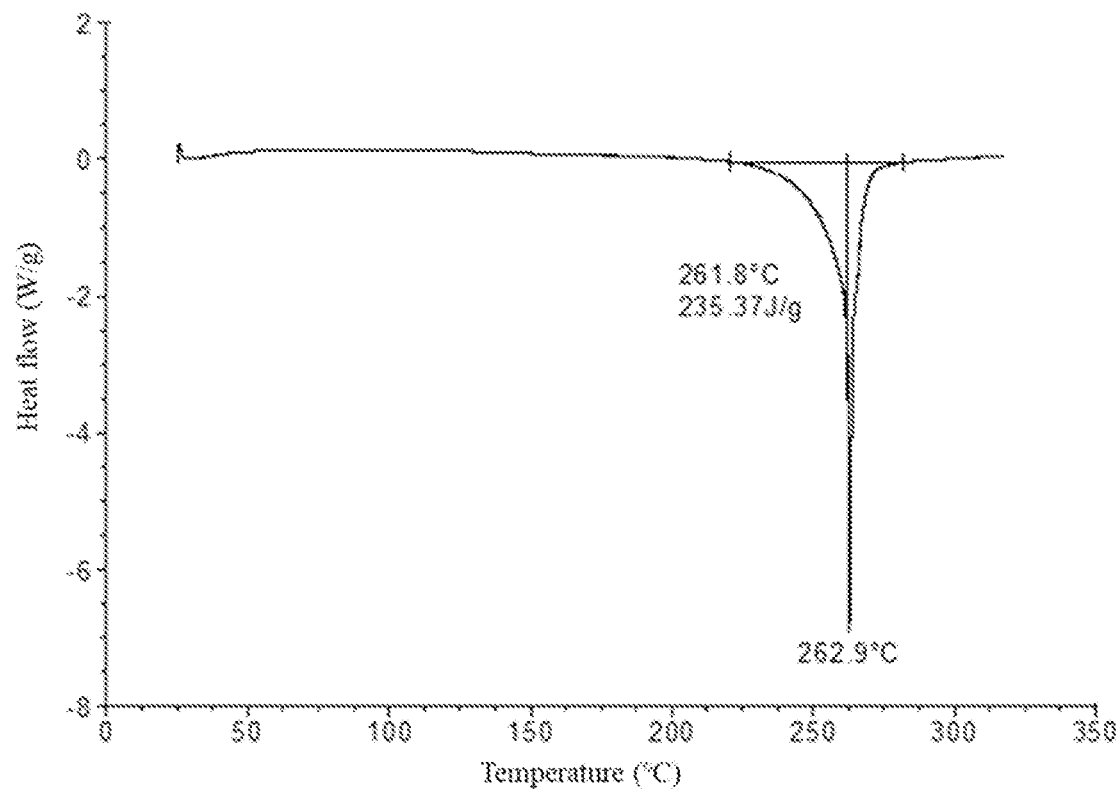
FIG. 5 is the DSC pattern of the crystal form E of the compound of formula (II).

12. The crystal form E as defined in claim 11, wherein the DSC pattern thereof is as shown in FIG. 5.

13. The crystal form E as defined in claim 7, wherein the crystal form E has a thermogravimetric analysis curve showing a weight loss of 1.72% occurred at 150.0° C.±3.0° C., a weight loss of 8.34% occurred at 230.0° C.±3.0° C. and a weight loss of 9.41% occurred at 280.0° C.±3.0° C.

Figure 6:
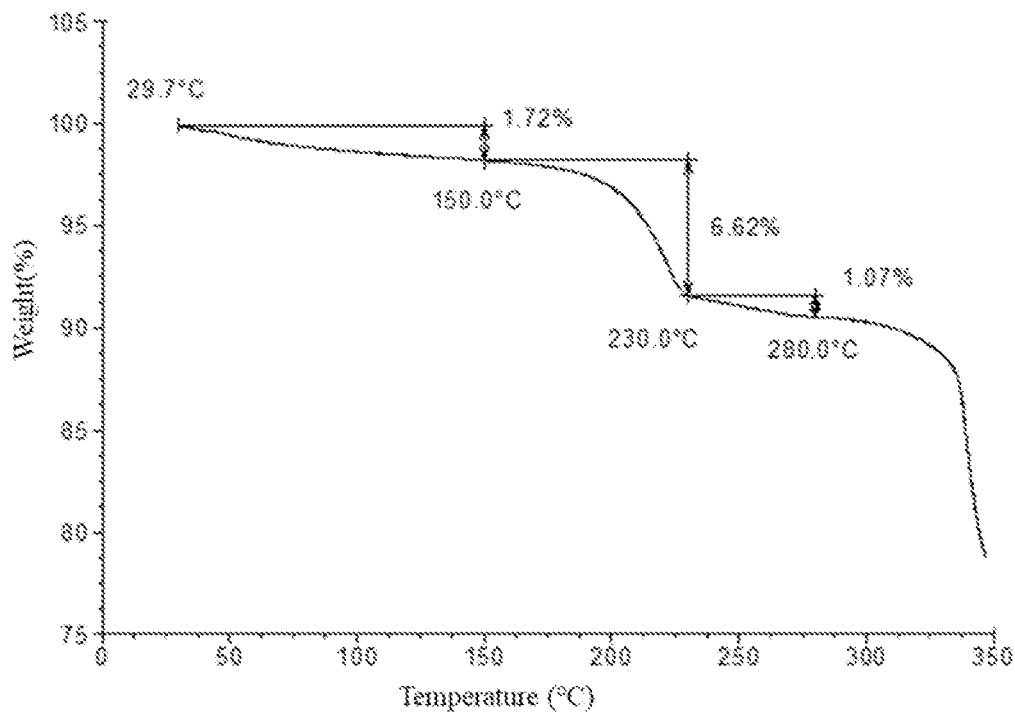
FIG. 6 is the TGA pattern of the crystal form E of the compound of formula (II).
Figure 7:
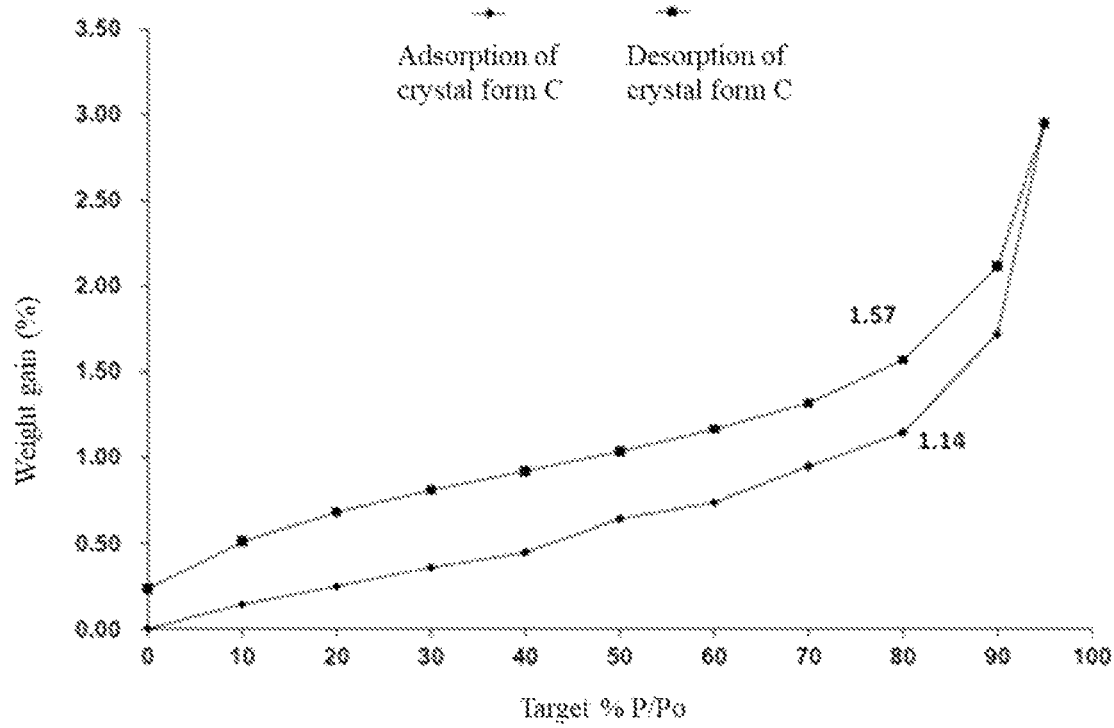
FIG. 7 is the DVS pattern of the crystal form C of the compound of formula (II).
Figure 8:
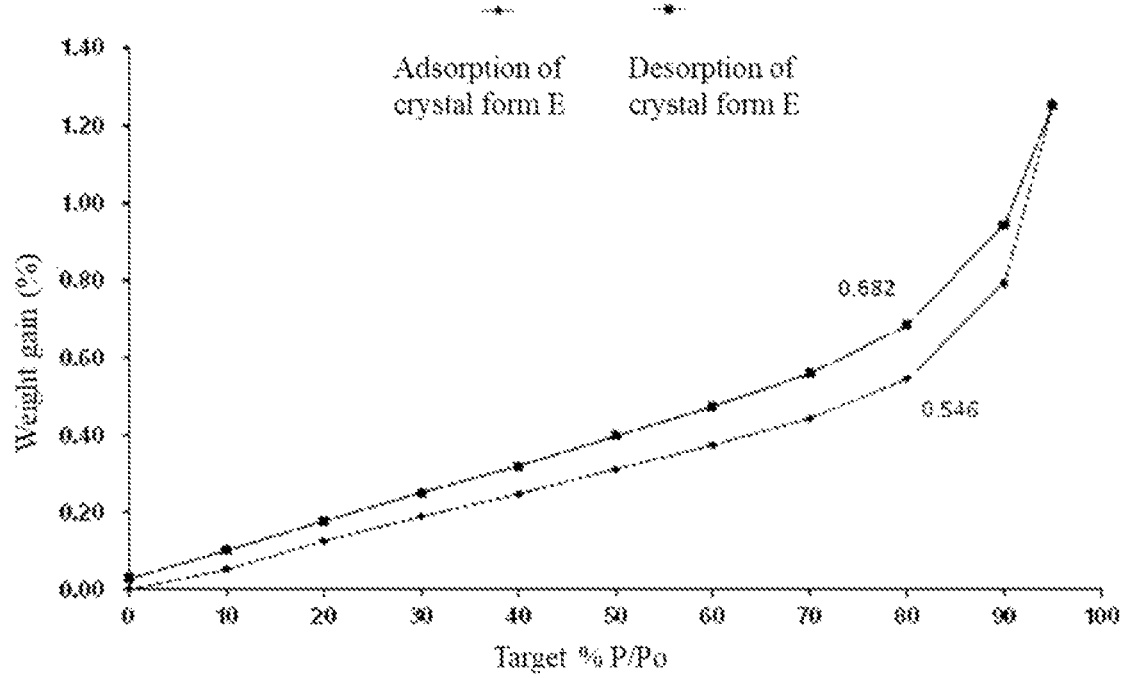
FIG. 8 is the DVS pattern of the crystal form E of the compound of formula (II).

14. The crystal form E as defined in claim 13, wherein the TGA pattern thereof is as shown in FIG. 6.

* * * * *